United States Patent [19]

Fujiwa et al.

[11] Patent Number: 4,735,749
[45] Date of Patent: Apr. 5, 1988

[54] PRODUCTION OF ACETYL COMPOUND

[75] Inventors: Takaaki Fujiwa; Hidetaka Kojima, both of Himeji, Japan

[73] Assignee: Daicel Chemical Industries, Ltd., Osaka, Japan

[21] Appl. No.: 914,684

[22] Filed: Oct. 2, 1986

Related U.S. Application Data

[63] Continuation of Ser. No. 710,875, Mar. 12, 1985.

[30] Foreign Application Priority Data

Mar. 22, 1984 [JP] Japan ................................. 59-55111

[51] Int. Cl.$^4$ ............................................. C07L 51/46
[52] U.S. Cl. .................................. 260/549; 260/546;
502/33; 502/53; 423/22
[58] Field of Search ................... 260/549, 546; 502/53, 502/33; 423/22

[56] References Cited

U.S. PATENT DOCUMENTS

| | | | |
|---|---|---|---|
| 4,131,640 | 12/1978 | Kutepow et al. | 423/22 |
| 4,252,741 | 2/1981 | Porcelli et al. | 260/549 |
| 4,434,241 | 2/1984 | Larkins | 260/549 |

*Primary Examiner*—Paul J. Killos
*Attorney, Agent, or Firm*—Flynn, Thiel, Boutell & Tanis

[57] ABSTRACT

A process is provided for producing an O-acetyl compound by carbonylating an O-methyl compound with carbon monoxide in the presence of a rhodium catalyst and an iodine compound, comprising (i) separating the reaction mixture formed in the carbonylation reaction step into a volatile component and a rhodium-containing catalyst solution, (ii) heat-treating the separated catalyst solution in the presence of a hydrogen-containing gas, and (iii) recirculating the hydrogenated catalyst solution to the carbonylation reaction step. According to this invention, it is possible to select a hydrogen treatment condition most suited for recirculation of a catalyst.

7 Claims, No Drawings

PRODUCTION OF ACETYL COMPOUND

This is a continuation of application Ser. No. 710,875, filed Mar. 12, 1985.

BACKGROUND OF THE INVENTION

1. Field of the Invention

This invention relates to a process for producing an O-acetyl compound such as acetic anhydride by reacting and O-methyl compound as a starting material, such as methyl acetate, with carbon monoxide by a catalytic reaction in which rhodium is used as a principal catalyst.

2. Description of the Prior Art

Acetic anhydride is used in quantity as a material for the production of cellulose acetate and, in addition, it is useful as a material for medicines, perfumes, dyes, etc.

Acetic anhydride has heretofore been produced industrially by a process in which ketene obtained by the thermal decomposition of acetic acid is reacted with acetic acid.

On the other hand, studies are being made actively to produce acetic anhydride by a reaction of carbon monoxide with methyl acetate or dimethyl ether. Although this reaction can proceed under a milder condition in a process in which rhodium is used as a principal catalyst than in processes in which other transition metal catalyst are used, it is necessary in order for this process to be actually used in the industry that a rhodium catalyst used in a carbonylation reaction can be recycled in an active form after it is separated from the desired product.

Japanese Patent Publication No. 2216/1983 (Japanese Patent Laid-Open No. 51036/1980) discloses a technique for preventing loss of the activity of a Group VIII noble metal catalyst in the separation step by improving the step of catalyst separation in the production of a carboxylic acid anhydride by carbonylation. This process comprises application of a partial pressure of hydrogen of at least 0.7 kg/cm$^2$ when the reaction mixture obtained in the carbonylation is separated into a volatile component and a catalyst solution. According to this process, it is preferred to maintain the partial pressure of carbon monoxide at 1.05 kg/cm$^2$ or above when a metallic promotor such as chromium is used, and consequently, as seen in the examples of this patent, a pressure-resistant vessel is necessary in the separation step (flash distillation), and it is probable that the compressed gas is carried away together with a volatile component.

A process is also known in which a considerable amount of hydrogen is incorporated in a reaction gas in the production of acetic anhydride from methyl acetate and carbon monoxide with the aid of a Group VIII noble metal catalyst (Japanese Patent Laid-Open No. 65709/1976). Although it is described that this process exerts an effect of preventing the formation of carbon dioxide, by-products such as ethylidene diacetate, acetaldehyde, acetone and methane, in addition to acetic acid mentioned in this publication, increase.

SUMMARY OF THE INVENTION

It is an object of this invention to provide a process for producing an O-acetyl compound by carbonylating an O-methyl compound with carbon monoxide in the presence of a rhodium catalyst and an iodine compound, whereby loss of the activity of the catalyst and the lowering of the selectivity for the reaction can be prevented and the catalyst solution can be recycled repeatedly.

This object has been achieved by (i) a step of separating the reaction mixture formed in the carbonylation reaction step into a volatile component and a rhodium-containing catalyst solution, (ii) a step of heat-treating the separated catalyst solution in the presence of a hydrogen-containing gas, and (iii) a step of recirculating the hydrogen-treated catalyst solution to the carbonylation step.

According to this invention, the hydrogen treatment step (ii) is provided as one separated from steps (i) and (iii), so that the degree of freedom in the selection of a treatment condition is higher, and the treatment is practiced even at atmospheric pressure. Although, when a hydrogen treatment is conducted at a hydrogen partial pressure in the separation step, its condition is limited inevitably by the condition for flash distillation, it is possible according to this invention to select a treatment condition most suited for recirculation of a catalyst.

In addition, since this hydrogen treatment is one separated from flash distillation or the carbonylation reaction, the amount of hydrogen used is such that it suffices for an amount of hydrogen required to maintain the activity of a catalyst, and there is no hydrogen that is carried away together with volatile component from a flash distillation apparatus or that is consumed in side reactions.

According this invention, it is thus possible to prevent side reactions, increase in the total pressure and consumption of hydrogen which otherwise are caused by the presence of hydrogen in the carbonylation step or the separation step; to make repeated recirculation of a carbonylation catalyst possible by effecting a separate step (ii) of hydrogen treatment while preventing a condition for hydrogen treatment and a condition for reaction or for separation being limited or affected by each other.

DETAILED DESCRIPTION OF PREFERRED EMBODIMENTS

The carbonylation of an O-methyl compound according to the process of this invention is presumed to proceed through the carbonylation of methyl iodide present in the reaction system. Namely, this invention is applied to reaction processes including a carbonylation reaction of methyl iodide and a conversion of acetyl iodide and an O-methyl compound into a desired O-acetyl compound under a substantially anhydrous condition, for example, the production of acetic anhydride from methyl acetate and the production of acetic anhydride and acetic acid from a mixture of methyl acetate and methanol.

A number of techniques which are the premise of this invention are known well in the above fields, and these techniques can be consulted when this invention is applied. Examples of the well-known techniques include the patent reference already cited and the literature cited therein.

Rhodium which is used as a principal catalyst in this invention can be added to a reaction system as a compound exemplified as follows: an inorganic rhodium salt such as rhodium chloride, rhodium bromide, rhodium iodide or rhodium nitrate; a rhodium carboxylate such as rhodium acetate; rhodium acetylacetonate, a rhodium amine complex salt; an organorhodium complex such as trichlorotrispyridinerhodium, hydridocarbonyltris(triphenylphosphine)rhodium, chlorotis(triphenylphosphine)rhodium or chlorocarbonylbis(triphenylphosphine)rhodium; and a cluster complex such as dodecacarbonyltetrarhodium. Althouh the amount of rhodium used is not necessarily limited strictly, it is used in a concentration of 0.1–50 mmol/l, preferably 10–30 mmol/l in terms of a concentration in a reaction solution.

In this reaction, a halide compound, especially an iodide compound, which is usually used in this field, is used, and the commonest typical example is methyl iodide. Although the amount of this compound is not necessarily limited, it is used in a concentration of 0.5–10 mol/l, preferably 1–5 mol/l in terms of a concentration in a reaction solution. It is possible to incorporate a variety of reaction accelerators in the rhodium-iodine compound (typified by methyl iodide), and typical examples of such accelerators include organophosphorus compounds and organonitrogen compounds. In addition, a process in which a combination of an organophosphorus compound with a metallic compound such as chromium hexacarbonyl is added is also known (Japanese Patent Laid-Open No. 115403/1976).

This invention is applicable to recirculation of a catalyst solution not only in a process in which the reaction of effected in the presence of an accelerator system formed by adding metallic aluminum to a reaction mixture containing a carboxylic acid (Japanese Patent Application No. 124342/1983, filed by the inventor of the present invention), but also in a process in which the reaction effected in the presence of a metallic co-catalyst such as aluminum, beryllium, titanium, zirconium, tin, vanadium, lithium, or thorium in the form of compounds.

The step of separating a reaction mixture formed in the carbonylation reaction step into a volatile component and a rhodium-containing catalyst solution can be practiced by using well-known techniques in flash distillation. In this step, most of the low-boiling compounds such as methyl iodide and methyl acetate are distilled off together with acetic anhydride and acetic acid.

Because the separated catalyst solution is substantially free of methyl iodide or methyl acetate though it contains part of the volatile components such as acetic anhydride or acetic acid, the formation of by-products such as methane is little when it is heat-treated with a hydrogen-containing gas. The hydrogen treatment is carried out by using a hydrogen-containing gas having a partial pressure of hydrogen of, usually, 0.2 kg/cm$^2$ or above and heating to a temperature of 100°–200° C.

When the temperature of the catalyst solution after flash distillation is 100° C. or above, additional heating is not necessary, and it is treated by contact with hydrogen of, for example, atmospheric pressure. The treatment time depends on the temperature, etc., and it is usually within the range of 0.1–2 hours, for example, 30 minutes. By incorporating the hydrogen treatment step, the catalyst activity which has been markedly lowered during the flash distillation can be recovered.

The formation of a by-product methane is suppressed markedly by adding carbon monoxide to the hydrogen-containing gas. For example, when comparison was made between a treatment with only hydrogen of 1 atm and a treatment with a gas mixture of hydrogen (0.7 atm) and carbon monoxide (0.3 atm), the formation of methane in the latter was decreased to one tenth or below of that in the former. Hydrogen containing carbon monoxide was excellent also in that the activity of a rhodium catalyst was recovered rapidly. Thus, it is preferred that the hydrogen treatment is carried out in the presence of carbon monoxide of a partial pressure of 0.1 kg/cm$^2$ or above. This is different from the case of the prior art cited above (column 12, line 20 of Japanese Patent Publication No. 2216/1983) wherein no change in the activity of a catalyst was recognized so long as the hydrogen partial pressure was maintained when the CO partial pressure in the separation zone was decreased to zero.

In order to confirm the effect of the hydrogen treatment performed after separation of volatile components, which is a feature of this invention, the infrared absorption spectrum of the rhodium catalyst solution was measured before and after the treatment. The inactive rhodium in a catalyst solution shows one absorption at 2085 cm$^{-1}$ and is presumed to be trans-form [Rh(CO)$_2$I$_4$]$^-$, while the rhodium in a catalyst solution heat-treated with a gas mixture of carbon monoxide (0.2 atm) and hydrogen (0.8 atm) at atmospheric pressure and 140° C. for 30 minutes does not show the above absorption but shows two new absorptions at 2049 cm$^{-1}$ and 1990 cm$^{-1}$, and is thought to be completely converted into an active species of cis-form [Rh(CO)$_2$I$_2$]$^{-1}$.

The carbonylation reaction of an O-methyl compound by using a recirculated hydrogen-treated catalyst solution was already described. Effects, such as suppression of side reactions, attained by carrying out the hydrogen treatment as a step separated from the main reaction were already described.

Because methyl acetate or acetic anhydride itself can serve as a solvent in the production of acetic anhydride by a carbonylation process, no solvent is added in most cases but some examples are also known in which a solvent is used. Particularly, an aliphatic carboxylic acid can play more than a role of an inert solvent in some cases, and it is used desirably in this invention frequently.

The starting materials to be carbonylated in this invention are those O-methyl compounds which form methyl iodide in the above reaction system, and the products are corresponding O-acetyl compounds. A typical example is the production of acetic anhydride by carbonylation of methyl acetate. Dimethyl ether can also be converted into acetic anhydride by carbonylation. In some cases, this invention is useful for the carbonylation of methanol.

Further, this invention is applicable to a carbonylation reaction of a carboxylic acid methyl ester, for example, formation of mixed anhydride of propionic and acetic acids (from which both propionic and acetic anhydrides can be formed by disproportionation) by carbonylation of methyl propionate.

The reaction temperature and pressure in the carbonylation reaction step can be selected appropriately with reference to the prior art. The reaction temperature is usually 130°–250° C., preferably 150°–200° C., the pressure of carbon monoxide during the reaction is 1–100 kg/cm$^2$G, preferably 5–100 kg/cm$^2$G, especially preferably 20–80 kg/cm$^2$·G.

Examples set forth below for the purpose of illustrating the present invention include batchwise reactions performed in an autoclave, and flash distillation and batchwise hydrogen treatment suitable for the reaction, and the pressure is expressed in terms of feed pressure. However, it is of course possible that the process of the present invention can be carried out continuously by using techniques known to the art.

The amounts of remaining methyl acetate in the reaction mixture and of acetic anhydride formed were determined by means of gas chromatography. The conversion of methyl acetate and yield of acetic anhydride were calculated according to the following equation:

$$\text{conversion (\%) of methyl acetate} = \frac{\text{amount of methyl acetate charged} - \text{amount of remaining methyl acetate in reaction mixture}}{\text{amount of methyl acetate charged}} \times 100$$

$$\text{yield of acetic anhydride (\%)} = \frac{\text{amount (mol) of acetic anhydride obtained}}{\text{amount (mol) of methyl acetate charged}} \times 100$$

The rate of reaction was calculated on the basis of a pressure drop during the initial stage of a reaction.

EXAMPLE 1

(Catalyst solution)

A 405 cc Hastelloy B autoclave was charged with 0.89 mmol of rhodium chloride trihydrate ($RhCl_3 \cdot 3H_2O$), 22 mg atom of aluminum metal powder, 4.5 ml of methyl iodide, 30 ml of acetic acid, and 30 ml of methyl acetate. After purging the atmosphere within the autoclave with carbon monoxide, the autoclave was pressurized with carbon monoxide to 40 kg/cm²G and then heated to 175° C. The reaction began at 175° C. and, after the absorption of gas occurred, the reaction was continued for 60 minutes. After the reaction, the autoclave was cooled and released from the remaining pressure, and the contents in the autoclave were transferred under a nitrogen stream to a flash distillation apparatus. The reaction mixture was flash-distilled at a bottom liquid temperature of 120°–138° C. until the volume of the solution was decreased to a half. The catalyst solution left after separating volatile components had a composition of 0.45 wt. % of methyl iodide, 0.5 wt. % of methyl acetate, 38.7 wt. % of acetic acid, and 51.2 wt. % of acetic anhydride. This catalyst solution was used in the experiments of Example 2 and the subsequent examples.

EXAMPLE 2

(Hydrogen treatment)

The catalyst solution of Example 1 was placed in an autoclave. After completely purging the space with a gas mixture (1 atm) of 4 parts by volume of hydrogen and 1 part by volume of carbon monoxide, the catalyst solution was heated to 140° C. and heat-treated in the presence of hydrogen for 30 minutes. The amount of methane produced during this treatment was 0.065 mmol.

(Reaction)

In order to carry out a carbonylation reaction with the same composition of a solution as in Example 1, the liquid component in the autoclave was completely distilled off in vacuum (5–10 mmHg, 80° C.). Then, a mixture of 30 ml of methyl acetate, 30 ml of acetic acid, and 4.5 ml of methyl iodide was placed in the autoclave and, after pressurizing the autoclave with carbon monoxide to 40 kg/cm² G, reacted at 175° C. for 1 hour. After cooling and releasing from the pressure, the reaction mixture was analyzed by means of gas chromatography. The conversion of methyl acetate was 83.2 % and the amount of acetic anhydride formed was 307.1 mmol. The rate of reaction in terms of a rate of formation of acetic anhydride per one mol of rhodium was 345.1 mol/mol Rh·hr. No ethylidene diacetate was formed.

EXAMPLE 3

(Comparative Example)

A carbonylation reaction was carried out in the same manner as in the reaction step of Example 2, except that the catalyst solution obtained in Example 1 was used without subjecting it to the hydrogen treatment of Example 2. The rate of reaction was 201.6 mol/mol Rh·hr, suggesting low activity. Example 4 (Comparative Example, reaction in the presence of hydrogen).

A carbonylation reaction was carried out in the same manner as in Example 3, except that a gas mixture of CO (35 kg/cm²G) and $H_2$ (5 kg/cm²) was used. The rate of reaction was on a high level, but 1.0 mmol of methane and 4.7 mmol of ethylidene diacetate were formed as by-products.

EXAMPLES 5 THROUGH 8

These examples were carried out in the same manner as in Example 2, except that the composition of a gas (1 atm in all of these examples) in the hydrogen treatment was varied. Treatment with hydrogen alone was possible as in Example 7. Table 1 shows the results.

EXAMPLE 9

The catalyst solution obtained in Example 1 was subjected to the same hydrogen treatment as that in Example 2 except that the autoclave was pressurized with a gas mixture of CO and $H_2$ (1:4) to 20 kg/cm²G, and the contents were heated at 130° C. for 30 minutes. In performing a carbonylation reaction, the distillation of a liquid component as in Example 2 was omitted, the autoclave was released from the gas, charged with 20 ml of methyl acetate and 4.5 ml of methyl iodide and pressurized with CO to 40 kg/cm²G, and the contents were reacted at 175° C. for 1 hour.

Although the result of the reaction in Example 9 can not be directly compared with the results of the reactions in Examples 2 through 8 because the compositions of the solutions are different, this experiment suggests a possibility that the hydrogen treatment can be performed under a pressure, for example, in a line for pumping the catalyst solution after flash distillation to a reaction vessel.

TABLE 1

| Example | Hydrogen treatment conditions | | | Methane formed $10^{-2}$ mmol | Results of reaction | | | |
| | Gas composition CO/H₂ | Pressure Kg/cm² G | Temperature °C. | | Conversion of methyl acetate (%) | Yield of acetic anhydride (%) | Rate of reaction | EDA mmol |
| --- | --- | --- | --- | --- | --- | --- | --- | --- |
| 2 | 1/4 | 0 | 140 | 6.5 | 83.2 | 73.7 | 345.1 | 0 |
| 3 | — | — | — | — | 57.1 | 46.8 | 201.6 | 0 |
| 4 | — | — | — | during reaction | 78.8 | 70.4 | 328.4 | 4.7 |

TABLE 1-continued

| | Hydrogen treatment conditions | | | | Results of reaction | | | |
|---|---|---|---|---|---|---|---|---|
| Example | Gas composition $CO/H_2$ | Pressure $Kg/cm^2$ G | Temperature °C. | Methane formed $10^{-2}$ mmol | Conversion of methyl acetate (%) | Yield of acetic anhydride (%) | Rate of reaction | EDA mmol |
| | | | | 100 | | | | |
| 5 | 1/3 | 0 | 140 | 1.45 | 80.0 | 75.0 | 335.1 | 0 |
| 6 | 1/7 | 0 | 140 | 8.0 | 81.5 | 78.5 | 312.9 | 0 |
| 7 | 0/1 | 0 | 140 | 24 | 78.4 | 66.1 | 292.0 | 0 |
| 8 | 3/1 | 0 | 140 | 0.72 | 66.7 | 58.0 | 259.7 | 0 |
| 9 | 1/4 | 20 | 130 | 5.0 | 81.5 | 81.2 | 245.1 | 0 |

What is claimed is:

1. In a process for preparing an O-acetyl compound by carbonylating, in a carbonylation reactor, an O-methyl material selected from the group consisting of methyl carboxylates, dimethyl ether and mixtures thereof with methanol, wherein said O-methyl material in the liquid phase is contacted with carbon monoxide gas, in the presence of a rhodium carbonylation catalyst and an iodine material that provides methyl iodide in the reaction liquid, whereby there is produced a liquid reaction product comprising volatile components and a non-volatile, rhodium catalyst-containing solution, then separating said volatile components from said liquid reaction product and separately recovering said non-volatile, rhodium catalyst-containing solution in which the rhodium catalyst has a reduced catalytic activity, the improvement for regenerating the rhodium carbonylation catalyst which consists essentially of the steps of: feeding sad non-volatile, rhodium catalyst-containing solution, substantially free of said volatile components, into a treatment zone and therein heating said catalyst solution at a temperature in the range of from 100° to 200° C., for from about 0.1 to about 2.0 hours, in contact with a gas having a partial pressure of hydrogen of at least 0.2 kg/cm² effective to restore the catalytic activity of the rhodium carbonylation catalyst whereby to obtain a hydrogen-treated catalyst solution in which the rhodium carbonylation catalyst is dissolved; and then recirculating the hydrogen-treated catalyst solution by feeding it from said treatment zone into the carbonylation reactor.

2. A process as claimed in claim 2 in which, in said treatment zone, said gas has a partial pressure of carbon monoxide of at least 0.1 kg/cm².

3. A process as claimed in claim 1 in which said gas consists of hydrogen and carbon monoxide.

4. A process as claimed in claim 3 in which said gas has a pressure of 1 atmosphere absolute.

5. A process as claimed in claim 3 in which the volumetric ratio of $CO/H_2$ in said gas is from 1/7 to 3/1.

6. A process as claimed in claim 1 in which said treatment zone is an autoclave.

7. In a process for preparing an O-acetyl compound by carbonylating, in a carbonylation reactor, an O-methyl material selected from the group consisting of methyl carboxylates, dimethyl ether and mixtures thereof with methanol, wherein said O-methyl material in the liquid phase is contacted with carbon monoxide gas, in the presence of a rhodium carbonylation catalyst and an iodine material that provides methyl iodide in the reaction liquid, whereby there is produced a liquid reaction product comprising volatile components and a non-volatile catalyst solution containing a soluble rhodium carbonylation catalyst displaying a characteristic IR absorption at 2085 cm$^{-1}$, separating said volatile components from said liquid reaction product and separately recovering said non-volatile, rhodium catalyst-containing solution, the improvement for regenerating the rhodium carbonylation catalyst which consists essentially of the steps of: feeding said non-volatile, rhodium-containing catalyst solution, substantially free of said volatile components, into a treatment zone and therein heating said catalyst solution at a temperature in the range of from 100° to 200° C., for from about 0.1 to about 2.0 hours, in contact with a gas having a partial pressure of hydrogen of at least 0.2 kg/cm² until the rhodium carbonylation catalyst shows two characteristic IR absorptions at 2049 cm$^{-1}$ and 1990 cm$^{-1}$ and the absorption at 2085 cm$^{-1}$ has disappeared whereby to obtain a hydrogen-treated catalyst solution in which the catalytic activity of the rhodium carbonylation catalyst has been restored; and the recirculating the hydrogen-treated catalyst solution by feeding it from said treatment zone into the carbonylation reactor.

* * * * *

UNITED STATES PATENT AND TRADEMARK OFFICE
CERTIFICATE OF CORRECTION

PATENT NO. : 4 735 749

DATED : April 5, 1988

INVENTOR(S) : Takaaki FUJIWA et al

It is certified that error appears in the above-identified patent and that said Letters Patent is hereby corrected as shown below:

Column 7, line 35; change "sad" to ---said---.

line 48; change "claim 2" to ---claim 1---.

Column 8, line 49; change "the" (first occurrence) to ---then---.

Signed and Sealed this

Twenty-ninth Day of November, 1988

*Attest:*

DONALD J. QUIGG

*Attesting Officer*      *Commissioner of Patents and Trademarks*